US011399819B2

(12) United States Patent
Sauer

(10) Patent No.: US 11,399,819 B2
(45) Date of Patent: Aug. 2, 2022

(54) PERCUTANEOUS SUB-XIPHOID LIFTING DEVICE AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

(*) Notice: Subject to any disclaimer, the term of this patent is extended or adjusted under 35 U.S.C. 154(b) by 434 days.

(21) Appl. No.: 16/456,264

(22) Filed: Jun. 28, 2019

(65) Prior Publication Data

US 2020/0015801 A1    Jan. 16, 2020

Related U.S. Application Data

(60) Provisional application No. 62/696,725, filed on Jul. 11, 2018.

(51) Int. Cl.
  *A61B 17/02* (2006.01)
  *A61B 17/00* (2006.01)

(52) U.S. Cl.
  CPC .......... *A61B 17/0281* (2013.01); *A61B 17/02* (2013.01); *A61B 17/0218* (2013.01); *A61B 2017/0046* (2013.01); *A61B 2017/00424* (2013.01); *A61B 2017/00477* (2013.01); *A61B 2017/0237* (2013.01)

(58) Field of Classification Search
  CPC . A61B 17/0281; A61B 17/0218; A61B 17/02; A61B 34/70; A61B 2017/0237
  See application file for complete search history.

(56) References Cited

U.S. PATENT DOCUMENTS

| | | | | |
|---|---|---|---|---|
| 4,181,123 A | * | 1/1980 | Crosby | ..................... A61B 1/07 600/184 |
| 4,319,562 A | * | 3/1982 | Crosby | ................ A61N 1/0587 600/564 |
| 5,846,191 A | * | 12/1998 | Wells | ....................... A61B 1/32 600/201 |
| 5,871,496 A | | 2/1999 | Ginn | |
| 5,931,777 A | * | 8/1999 | Sava | ...................... A61B 17/02 600/213 |
| 6,074,344 A | * | 6/2000 | Paschall, Jr. | ........... A61B 17/02 600/210 |

(Continued)

FOREIGN PATENT DOCUMENTS

WO    WO2009004610    1/2009

OTHER PUBLICATIONS

Journal: RRD 2011 Shimizu, Interactive Cardiovascular and Thoracic Surgery: 12 (2011) 998-1001, Publisher: Oxford University Press, worldwide doi:10.1510/icvts.2010.264929.

*Primary Examiner* — David W Bates
(74) *Attorney, Agent, or Firm* — Michael E. Coyne

(57) ABSTRACT

A percutaneous sub-xiphoid lifting device is disclosed. Also disclosed is a percutaneous sub-xiphoid lifting device including a beam assembly and a lifting assembly. The percutaneous sub-xiphoid lifting device includes a pair of beams, pivotably coupled at a distal end and configured to be releasably attached to the lifter block coupled to a handle. The percutaneous sub-xiphoid lifting device may further include a light source used for improved visualization. A method of using the percutaneous sub-xiphoid lifting device for increasing space beneath the sternum during a minimally invasive surgical procedure is also disclosed.

14 Claims, 15 Drawing Sheets

(56) References Cited

U.S. PATENT DOCUMENTS

| | | | |
|---|---|---|---|
| 6,083,153 A * | 7/2000 | Rullo | A61B 17/02 600/217 |
| 6,102,854 A * | 8/2000 | Cartier | A61B 1/32 600/210 |
| 6,199,556 B1 * | 3/2001 | Benetti | A61B 17/02 128/898 |
| 6,354,994 B1 * | 3/2002 | Rullo | A61B 17/02 600/217 |
| 6,428,180 B1 * | 8/2002 | Karram | A61B 5/0059 362/109 |
| 7,582,058 B1 * | 9/2009 | Miles | A61B 5/296 600/202 |
| 8,906,048 B2 | 12/2014 | Lin | |
| 10,052,089 B2 * | 8/2018 | Guilford | A61B 17/02 |
| 10,159,520 B2 * | 12/2018 | Krickeberg | A61G 13/0081 |
| 11,173,040 B2 * | 11/2021 | Abdou | A61F 2/4611 |
| 2003/0094180 A1 | 5/2003 | Benetti | |
| 2004/0129109 A1 * | 7/2004 | Phillips | A61B 17/02 74/577 M |
| 2005/0015013 A1 * | 1/2005 | Greszler | A61B 17/02 600/476 |
| 2005/0148824 A1 * | 7/2005 | Morejohn | A61B 17/0281 600/208 |
| 2006/0129238 A1 * | 6/2006 | Paltzer | A61F 2/447 623/17.11 |
| 2007/0021655 A1 * | 1/2007 | Sayeg | A61B 17/02 600/210 |
| 2007/0106123 A1 * | 5/2007 | Gorek | A61B 17/7082 600/210 |
| 2007/0129608 A1 * | 6/2007 | Sandhu | A61B 17/02 600/219 |
| 2007/0213596 A1 * | 9/2007 | Hamada | A61B 17/02 600/219 |
| 2007/0250100 A1 * | 10/2007 | Schon | A61M 25/0668 606/191 |
| 2008/0108877 A1 * | 5/2008 | Bayat | A61B 1/32 600/214 |
| 2011/0009899 A1 * | 1/2011 | Picha Muthu | A61B 17/02 606/207 |
| 2017/0007287 A1 * | 1/2017 | Malewicz | A61B 17/3415 |
| 2018/0200508 A1 * | 7/2018 | Sauer | A61N 1/372 |
| 2019/0038272 A1 * | 2/2019 | Whitman | A61B 90/30 |
| 2019/0076161 A1 | 3/2019 | Chin | |

* cited by examiner

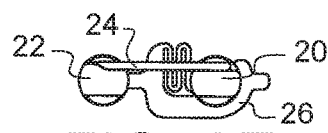
FIG. 3E
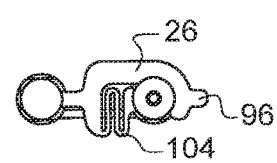
FIG. 3F
FIG. 3B  FIG. 3A  FIG. 3C  FIG. 3D

PERCUTANEOUS SUB-XIPHOID LIFTING DEVICE AND METHODS THEREOF

RELATED APPLICATIONS

This patent application claims priority to U.S. Provisional Patent Application No. 62/696,725 filed Jul. 11, 2018 and is entitled "PERCUTANEOUS SUB-XIPHOID LIFTING DEVICE AND METHODS THEREOF." The entire 62/696,725 application is hereby incorporated by reference in their entirety.

FIELD

The claimed invention relates to percutaneous sub-xiphoid lifting devices, and more specifically to surgical devices used in internal thoracic artery harvesting, epicardial lead placement, and other minimally invasive surgical procedures.

BACKGROUND

Minimally invasive surgical approaches are gaining increased interest in relation to coronary procedures. Coronary revascularization or grafting of the internal thoracic artery (ITA) has shown superior long-term patency and improved patient outcome in coronary artery bypass graft (CABG) surgeries. While conventional approaches to ITA harvesting have included median sternotomy or multiple thoracoports, a minimally invasive approach is desirable. A minimally invasive procedure related to revascularization using either the left or right internal thoracic artery (ITA), or the left or right internal mammary artery (IMA) utilizes a rib cage lifting technique, where increased surgical space is gained by accessing the internal thoracic arteries via incision at the subxiphocostal region.

Upon harvesting either the left internal thoracic artery (LITA) or the right internal thoracic artery (RITA) anastomoses to the left anterior descending (LAD) coronary artery and to the right coronary artery (RCA), respectively, can be performed without cardiopulmonary bypass (CPB). A significant advantage of this approach is that a perfectly harvested ITA graft can be perfectly anastomosed to the usual site on the LAD artery, or onto the RCA artery. A minimally invasive ITA harvesting procedure involving rib cage lifting also results in superior cosmetic results, is reasonably painless, and the arterial grafting can be accomplished on the beating heart. Recent approaches of minimally invasive ITA harvesting surgical techniques have been shown to result in increased effective length of ITA bypasses, reduced operation times, and improved patient recovery.

While less invasive surgical approaches for ITA harvesting and CABG have shown promise, visualization, maintenance of insufflation, and distal suturing of a coronary anastomosis in totally endoscopic coronary artery bypass grafting on the beating heart is technically demanding. There is a need for larger working spaces to accommodate an increased range of motion during surgical procedures, as well as room for additional surgical tools, such as endoscopes, suturing tools, and the like. However, achieving an increased working space should ideally preserve chest wall integrity and avoid CPB. Likewise, a minimally invasive surgical approach should not compromise the reliability of a cardiac repair.

Therefore, there exists a need for minimally invasive surgical devices and methodology applicable to ITA harvesting and other surgical procedures such as epicardial lead placement and others that increase operable space for harvesting and anastomosis and other surgical procedures, reduce operating time, and improve patient outcome during minimally invasive cardiac procedures and other surgical procedures.

SUMMARY

A percutaneous sub-xiphoid lifting device is disclosed. The percutaneous sub-xiphoid lifting device includes a handle, a lifter block coupled to the handle, a first beam having a proximal end coupled to the lifter block, and a second beam having a proximal end coupled to the lifter block.

A method of percutaneous sub-xiphoid lifting is also disclosed. This method includes creating a first incision and a second incision below a sternum, pushing a distal end of a percutaneous sub-xiphoid lifting device beneath the sternum, and lifting the percutaneous sub-xiphoid lifting device in an anterior direction so that increased space is created by lifting the sternum away from a diaphragm to increase space for a minimally invasive surgical procedure.

Another percutaneous sub-xiphoid lifting device is disclosed. The percutaneous sub-xiphoid lifting device includes a handle, a lifter block coupled to the handle, a first beam having a proximal end coupled to the lifter block, a second beam having a proximal end coupled to the lifter block, and a light source.

BRIEF DESCRIPTION OF DRAWINGS

FIGS. 3A, 3B, 3C, 3D, 3E, and 3F are front, left side, right side, rear, top, and bottom elevational views, respectively, of a beam assembly of the percutaneous sub-xiphoid lifting device of FIG. 1.

Figure 1:
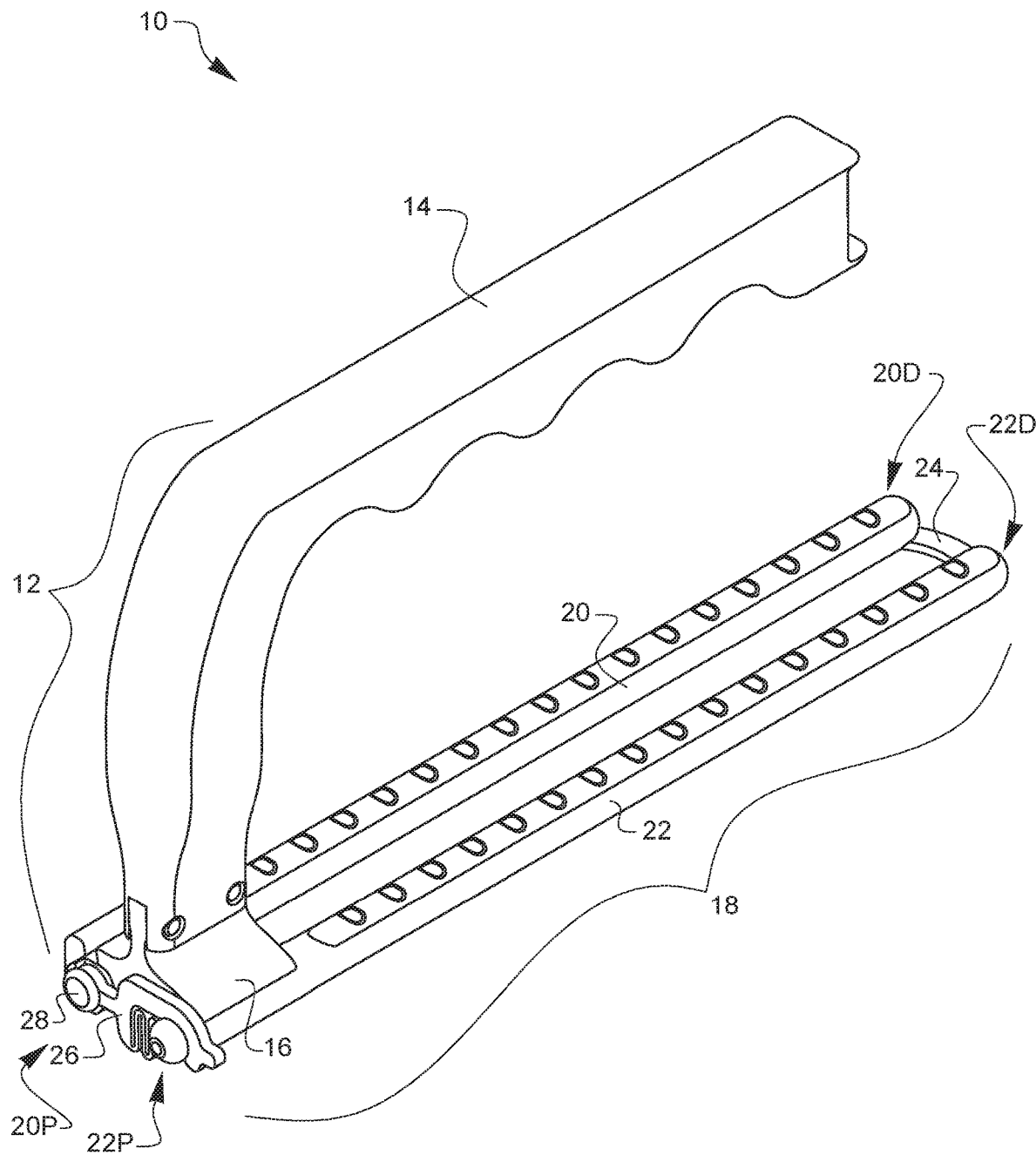
FIG. 1 is a proximal-top-right perspective view of an embodiment of a percutaneous sub-xiphoid lifting device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a proximal-top-right perspective view of an embodiment of a percutaneous sub-xiphoid lifting device. The percutaneous sub-xiphoid lifting device 10 includes a lifter assembly 12, which includes a handle 14 with an attached lifter block 16. The percutaneous sub-xiphoid lifting device 10 also includes a beam assembly 18, which includes a first beam 20 and a second beam 22 connected at their respective distal ends 20D, 22D by a swivel link 24. The beam assembly 18 is configured to be releasably engaged into the lifter block 16 portion of the lifter assembly 12. The first beam 20 and the second beam 22 are pivotably coupled by a swivel link 24 connected to the distal end 20D of the first beam 20 and the distal end 22D of the second beam 22. A latch 26 is attached to the proximal end 20P of the first beam 20 and is configured to rotate or pivot around a pivot pin 28 and temporarily hold the second beam 22 in place once the first beam 20 and the second beam 22 have been fully inserted into the lifter block 16. It should be noted that while this is one embodiment of a percutaneous sub-xiphoid lifting device 10, it is not meant to be a limiting example. Other embodiments of this device may include a beam assembly that is permanently attached to a lifter assembly or include beams that are not pivotably or rotatably coupled. While this embodiment is illustrated in a manner that allows for approximately 90-degree rotation or pivot between the first beam 20 and the second beam 22, other embodiments may pivot further than 90 degrees, for example, 180 degrees or more. Likewise, the first beam and second beams of an alternate embodiment may be coupled in a manner that allows for additional degrees of freedom of movement and may swivel in multiple directions and to further extents than 90 degrees or 180-degree angles between the first beam and the second beam. Either one or both ends of the swivel link 24 may pivot. Alternative ways of coupling the beams may also be used, such as hinges, additional beams, fixed shims, support members, or others known by those skilled in the art. Other embodiments for beams may be used in these devices as well. While the beams shown in this embodiment of a percutaneous sub-xiphoid lifting device 10 are cylindrical rods, other beams may be used in alternate embodiments, such as flat shims, rectangular beams, flat blades, or others known by those skilled in the art. The beams may also be arranged in orientations other than parallel.

Figure 2:
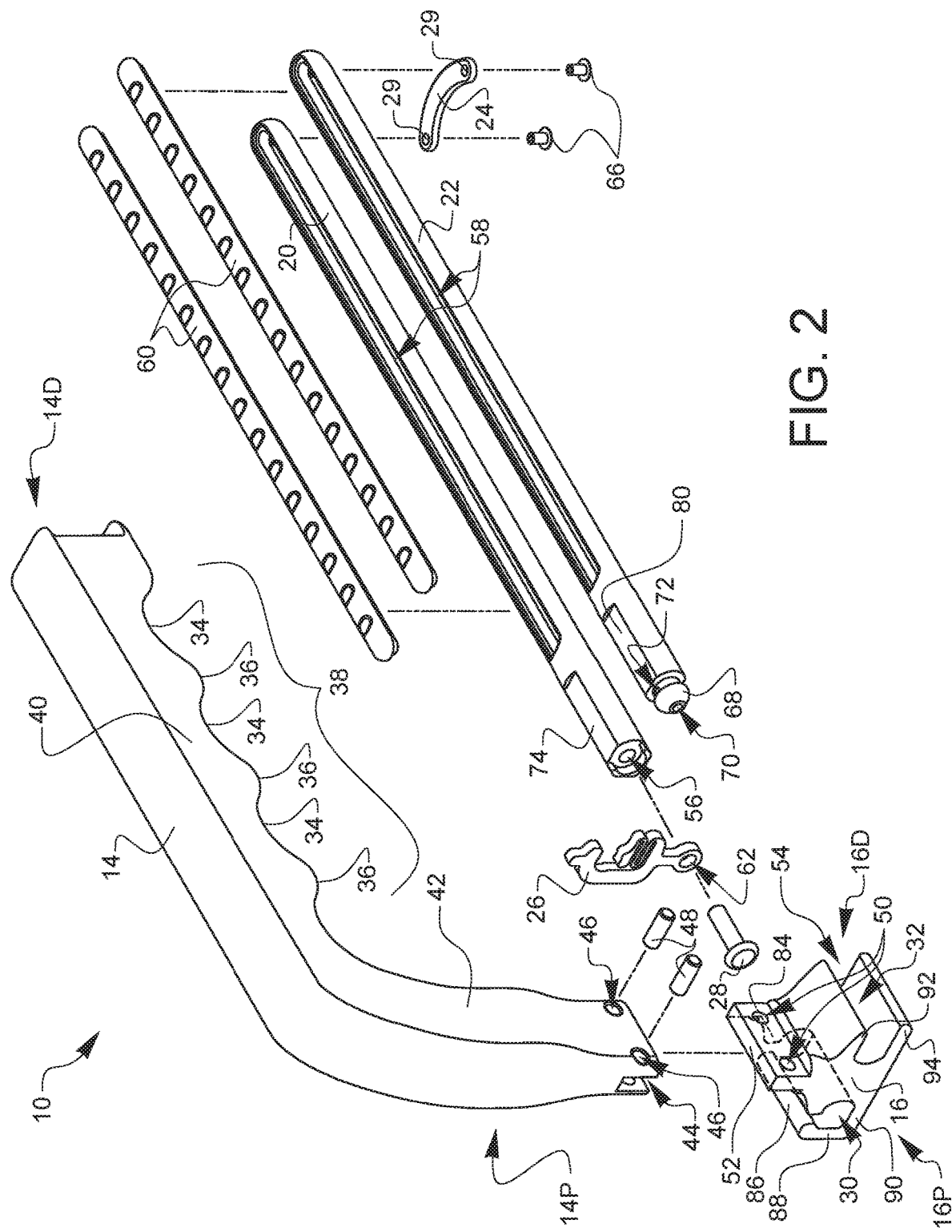
FIG. 2 is an exploded view illustrating the assembly of the percutaneous sub-xiphoid lifting device of FIG. 1.

FIG. 2 is an exploded view illustrating the assembly of the percutaneous sub-xiphoid lifting device of FIG. 1. The handle 14 defines several recesses 34 and protrusions 36 for forming an ergonomic grip 38 for improved grip and ease of operation by a surgeon or surgical assistant. The ergonomic grip 38 is located in an upper portion 40 of the handle 14 beginning at a distal end 14D. The distal end 14D of the handle 14 may include hardware, recessed features, or other means for attaching a surgical instrument holder or other holding device (not shown in this view) to the distal end 14D of the handle 14. The handle 14 curves towards a lower portion 42 at a proximal end 14P of the handle 14. The lower portion 42 of the handle 14 further defines a notch 44 and two holes 46 configured to receive pins 48. There are also corresponding holes 46 on the opposite side of the handle 14 not completely shown in this view. The notch 44 is configured to accept a lifter block leg 52 of the lifter block 16 and the holes 46 in the handle 14 are aligned with corresponding holes 50 in the leg 52 of the lifter block 16. These holes 46, 50 are configured to receive two pins 48 that stake and permanently fix the lifter block 16 to the handle 14. The lifter block 16 has a proximal end 16P and a distal end 16D. Other means of attachment of a lifter block to the handle may be known to those skilled in the art, such as screw fastening, brazing or welding. Other embodiments may have a single element having both a handle and a structure similar to a lifting block.

The beam assembly 18 includes the first beam 20 and the second beam 22 which are rotatably coupled by a swivel link 24 at the distal end 20D of the first beam 20 and at the distal end 22D of the second beam 22. Either end of the swivel link 24 are attached to the first beam 20 and the second beam 22 with two rivets 66 which are inserted through holes 29 and into a hole on each of the first beam 20 and the second beam 22 (not shown in this view). The swivel link 24 may be attached by other means known to those skilled in the art, for example, screws. The swivel link 24 may also be considered a hinge, and as shown in this embodiment is a flat, arc-shaped component having connection points on either end. Alternate embodiments may be straight, curved, triangular, partially rectangular, other shapes, or a combination thereof. The swivel link may have a sharpened side or edge or other feature useful in the aid of clearing tissue or separating tissue. Each beam 20, 22 has a beam channel 58 configured to receive a soft insert 60. The soft insert 60 is made of a soft material for the purpose of reducing or minimizing trauma to surrounding tissue during use of the percutaneous sub-xiphoid lifting device 10. The soft inserts 60 provide an atraumatic anterior facing surface and may also enhance stability of beam when held against tissue, depending on the condition of the surrounding tissue and the particular requirements of the surgical procedure. While the embodiment shown uses a soft plastic or rubber material, an alternate soft insert could be composed of silicone, another soft elastomer formulation, or a plastic. Other embodiments may not have soft inserts.

A latch 26 is attached at the proximal end 20P of first beam 20, by inserting a pivot pin 28 into a first beam hole 56 through a hole 62 in the latch 26. The latch 26 is shaped and configured to rotate around the pivot pin to not create an obstruction during insertion of the first beam 20 into the keyed opening 30. The second beam 22 includes an endcap 68 at the proximal end 22P of the second beam 22. The endcap 68 defines a side aperture 72 and an end aperture 70 that are configured to receive a suture or guide wire to facilitate engaging the percutaneous sub-xiphoid lifting device 10 into one or more incisions in a patient (not shown in this view).

During use in a procedure the percutaneous sub-xiphoid lifting device 10 is assembled from the lifter assembly 12 and the beam assembly 18. The lifter block 16 further defines a keyed opening 30 and a slot opening 32. The keyed opening 30 is configured to slidably receive the first beam 20, and the slot opening 32 is configured to receive the second beam 22 via either slidable engagement towards the distal end 16D of the lifter block 16, or rotatable engagement into the open side 54 of the slot opening 32. The lifter block 16 also includes a handle support 84 on either side of the lifter block configured for improved alignment during set up or assembly of the percutaneous sub-xiphoid lifting device 10. The lifter block 16 has a keyed opening upper support 86, a keyed opening leg 88, and a keyed opening lower support 90, which further define the keyed opening 30. These features are configured to receive the proximal end 20P of the first beam 20 into the keyed opening 30 at the proximal end 16P of the lifter block 16 and coordinate with several facets 74, 80 (later described in regard to FIGS. 3A-3F) on the first beam 20. This keying feature ensures proper orientation and configuration of the lifter assembly 12 with the beam assembly 18 during the use of the percutaneous sub-xiphoid lifting device 10 during surgical procedures.

The lifter block 16 also has a slot opening upper support 92 and a slot opening lower support 94, which further define the slot opening 32. The slot opening 30 is configured to receive the second beam 22 via sliding the proximal end 22P of the second beam 22 into the slot opening 32 from the distal end 16D of the lifter block 16 towards the proximal end 16P of the lifter block 16, or via rotatable engagement into the open side 54 of the slot opening 32. Once both the first beam 20 and the second beam 22 are fully inserted into the lifter block 16, the latch 26 can be rotated around the pivot pin 28 to attach onto the endcap 68 and hold the beam assembly 18 in the lifter assembly 12 until disengagement is desired.

While the embodiment for the percutaneous sub-xiphoid lifting device 10 illustrated in FIGS. 1 and 2 has a separate lifter assembly 12 and beam assembly 18, other embodiments may be a singular device, having a beam assembly portion permanently attached to the lifter portion. In other embodiments, only the first beam may be permanently attached to the lifter portion while the second beam rotatably engages with a slot opening on the lifter block. Other embodiments may be combinations of the illustrated embodiment, the alternate embodiments discussed herein, or combinations thereof.

FIGS. 3A, 3B, 3C, 3D, 3E, and 3F are front, left side, right side, rear, top, and bottom elevational views, respectively, of a beam assembly of the percutaneous sub-xiphoid lifting device of FIG. 1. While most elements of the beam subassembly have been discussed above in regard to FIGS. 1 and 2, the elevational views further illustrate key features of this embodiment of the beam assembly 18. FIG. 3A is a front view of the beam assembly 18 of the percutaneous sub-xiphoid lifting device 10 of FIG. 1. FIG. 3A illustrates the anterior facing surface of the beam assembly 18, which is the surface that contacts the patient beneath the sternum and faces in an anterior direction during use. FIGS. 3A-3F also illustrate additional features that ensure proper orientation and configuration of the lifter assembly 12 with the beam assembly 18 during the use of the percutaneous sub-xiphoid lifting device 10. A first beam top facet 74, first beam bottom facet 76, and first beam side facet 78 are shown in FIGS. 3A, 3D and 3B, respectively. These facets 74, 76, 78 are configured to interface with the keyed opening 30 in the lifter block 16 as shown in and described in regard to FIGS. 1 and 2. The flat areas or facets 74, 76, 78 in an otherwise round first beam 20 correspond with the flat areas or surfaces in the keyed opening 30 to both preserve the appropriate orientation when the beam assembly 18 is slidably engaged into the lifter assembly 12 and limit insertion to a depth defined by the facets 74, 76, 78 as described above. A second beam top facet 80 and second beam bottom facet 82 are shown in FIGS. 3A and 3D respectively. These facets 80, 82 are configured to interface with the slot opening 32 in the lifter block 16 as shown in and described in regard to FIGS. 1 and 2. The flat facets 80, 82 in an otherwise round second beam 22 correspond with the flat surfaces in the slot opening 32 to both preserve the appropriate orientation when the beam assembly 18 is slidably or rotatably engaged into the lifter assembly 12. These facets 80, 82 also define a depth and limit insertion of the second beam 22 into the lifter block 16. While facets or flat areas on the cylindrical beams are shown in this embodiment, other keyed features in the beams and in the lifter block may be utilized in alternate embodiments.

Figure 4A:
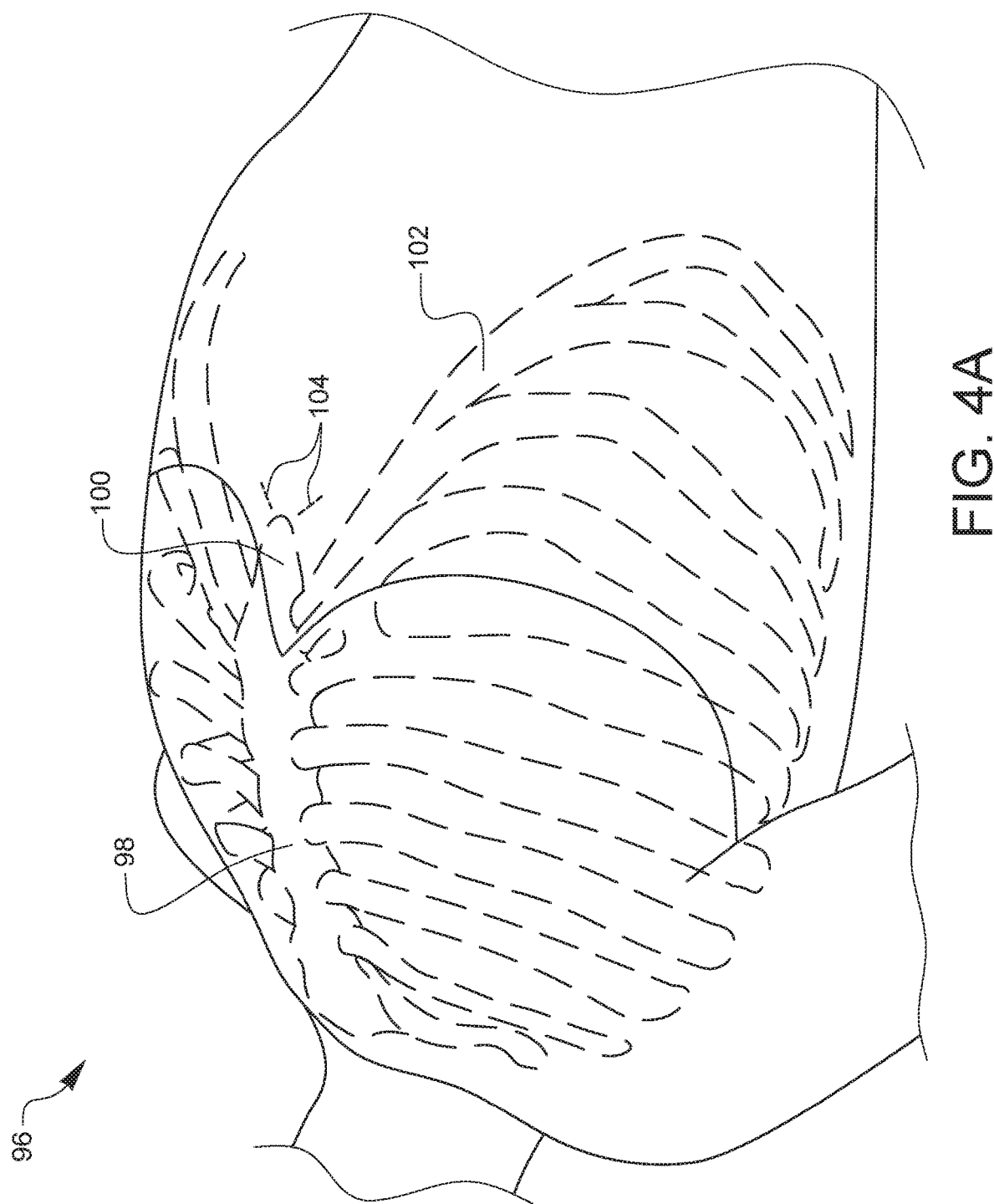
FIGS. 4A-4H and FIGS. 4J-4M are a series of top-right perspective views illustrating the use of the percutaneous sub-xiphoid lifting device of FIG. 1. FIG. I was intentionally omitted to avoid confusion with numeral one.
Figure 4B:
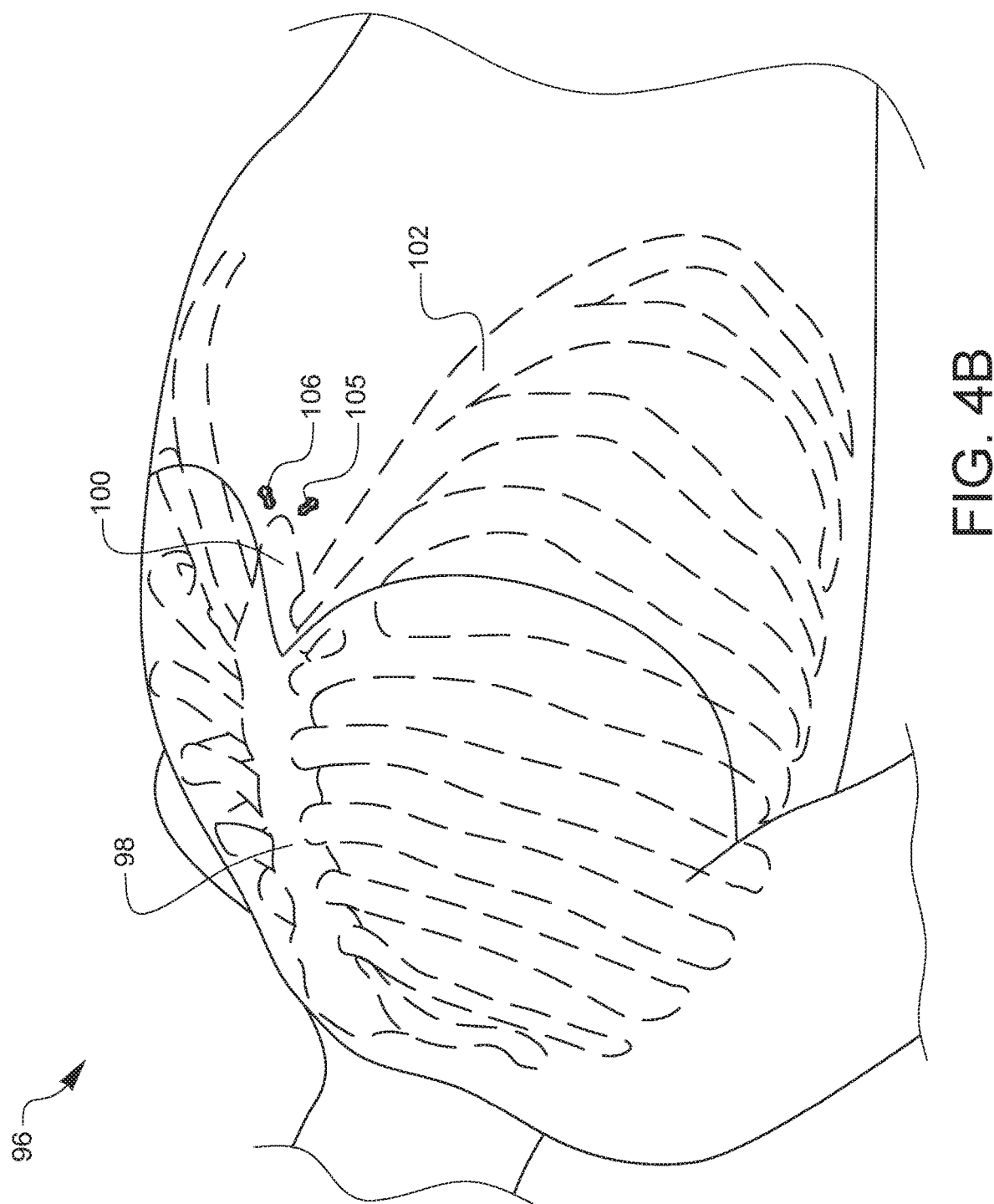
Figure 4C:
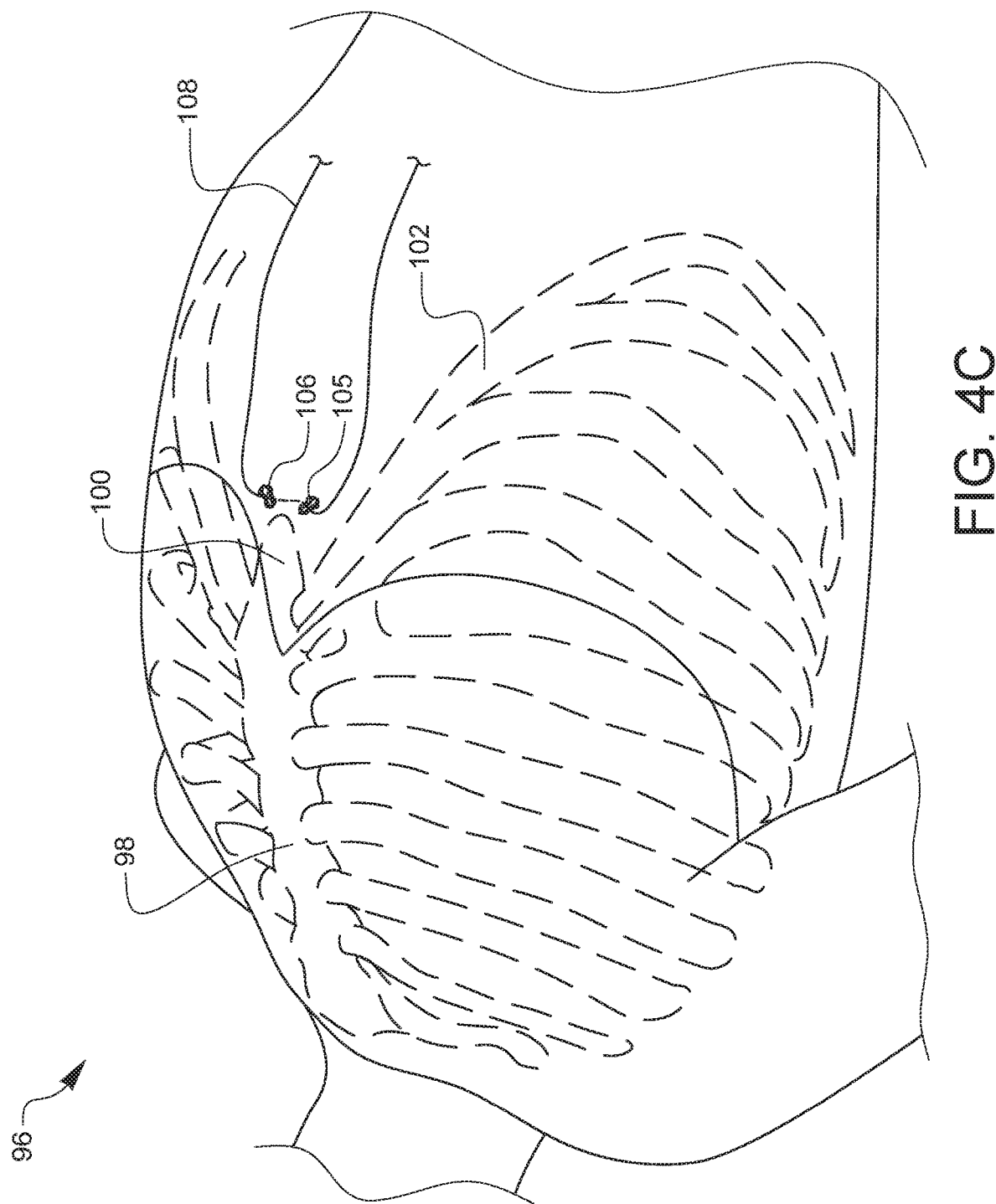

FIGS. 4A-4H and FIGS. 4J-4M are a series of top-right perspective views illustrating the use of a percutaneous sub-xiphoid lifting device. FIG. 4A illustrates a patient 96 prepared for a minimally invasive surgical procedure requiring increased subxiphoid access. Indicated in this view are the relative locations of the sternum 98, the xiphoid 100 or xiphoid process, which is the lower part of the sternum 98. Also shown are the ribcage 102 or the patient and several preparatory incision locations 104 below the sternum 98 and in proximity to the xiphoid 100. FIG. 4B is a perspective view illustrating the location of a first incision 105 and a second incision 106 placed below the xiphoid 100. FIG. 4C illustrates a guidewire 108 placed into the first incision 105, below the skin and out of the second incision 106 for the purpose of guiding a percutaneous sub-xiphoid lifting device through the incisions 105, 106 in subsequent steps. While a guidewire 108 is shown in FIG. 4C, any suitable means of threading the device through the incision sites such as suture or thread or other means may be employed by one skilled in the art.

Figure 4D:
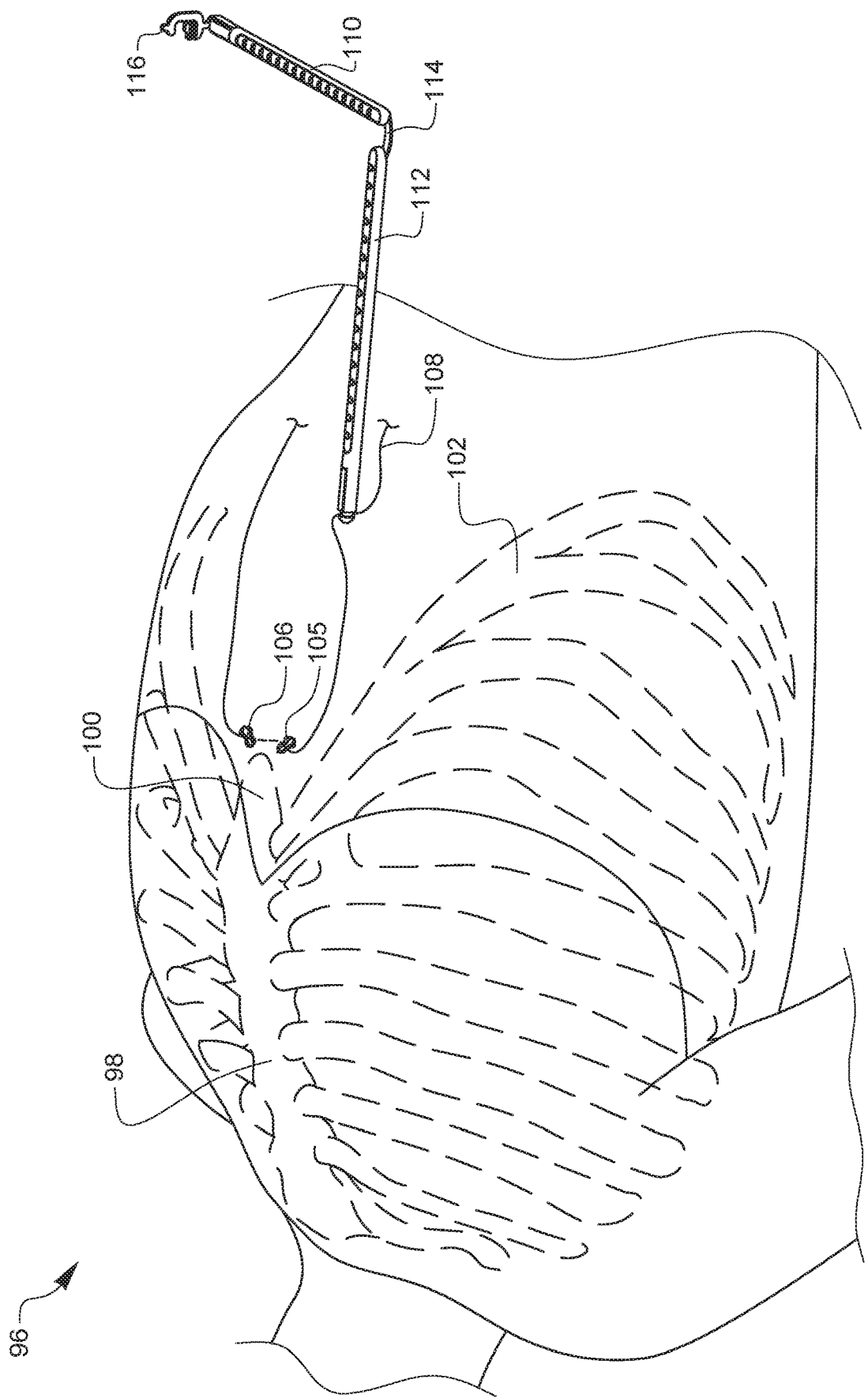
Figures 4E, 4F:
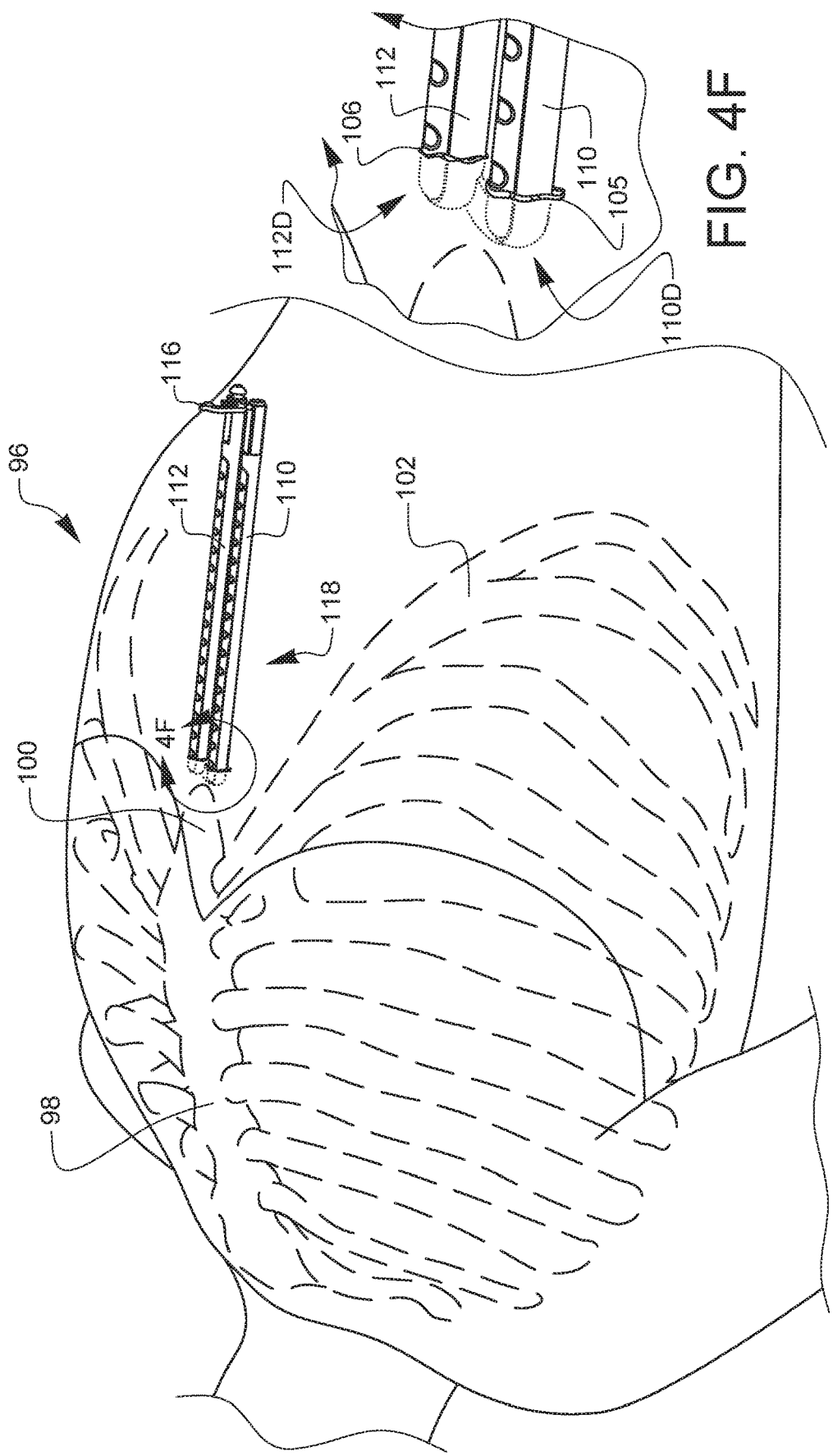

FIG. 4D illustrates a step in the use of a percutaneous sub-xiphoid lifting device wherein the guidewire 108 already threaded through the incisions 105, 106 is attached to the second beam 112 of the percutaneous sub-xiphoid lifting device for the purpose of guiding the second beam 112 and first beam 110 into the first incision 105, below the skin and out of the second incision 106. In this view, the swivel link 114 is shown connecting the first beam 110 and the second beam 112 with the latch 116 shown in an opened or unlatched position. While a guide wire attached to the endcap (not detailed in this view) of the second beam 112 has been used to facilitate maneuvering the second beam 112 into one incision 105, below the skin and out of the other incision 106, other methods of maneuvering the second beam through the first incision 105 and second incision 106 may be used, such as manual guidance by graspers or by other known methods. In FIG. 4E, the beam assembly 118 including the first beam 110 and the second beam 112 are shown in a parallel arrangement with the distal ends 110D, 112D of each of the first beam 110 and the second beam 112 threaded though and placed into the incisions 105, 106 below the xiphoid 100. FIG. 4F shows an enlarged view of this end of the beam assembly 118.

Figure 4G:
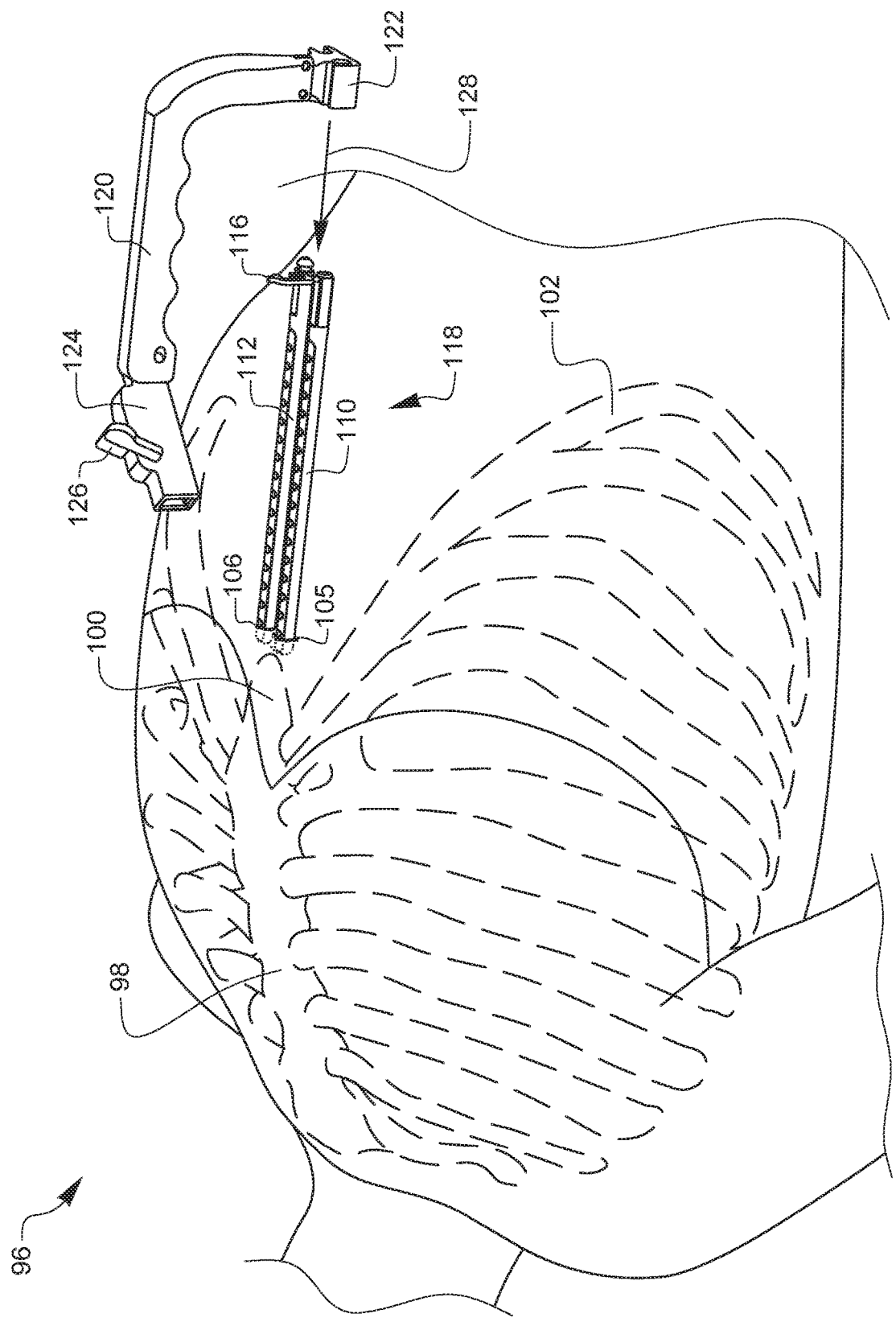

In FIG. 4G the ends of the beam assembly 118 are positioned in the two incisions 105, 106 as described previously in regard to FIGS. 4E and 4F. The lifter assembly 120 is moved in a direction 128 to attach the beam assembly 118 to the lifter assembly 120. Once the second beam 112 is passed through both incisions 105, 106, the second beam 112 can be rotatably engaged in the lifter block 122 and secured with the latch 116 as previously described herein. This means of temporary attachment has been described previously in regard to other embodiments of a percutaneous sub-xiphoid lifting device. This embodiment of a percutaneous subxiphoid lifting device 130 has a beam assembly 118, a lifter assembly 120, and an instrument adapter 124 with a lever lock 126 attached to the lifter assembly 120 for later attachment to and stabilization by a surgical equipment holder. The instrument adapter 124 may be attached by any number of fastening methods including welding, brazing fastening by screws or bolts, or a combination thereof. The latch 116 is in an open position and allows for slidable engagement of the beam assembly 118 into the lifter block 122 of the lifter assembly 120 of the percutaneous subxiphoid lifting device 130.

Figure 4H:
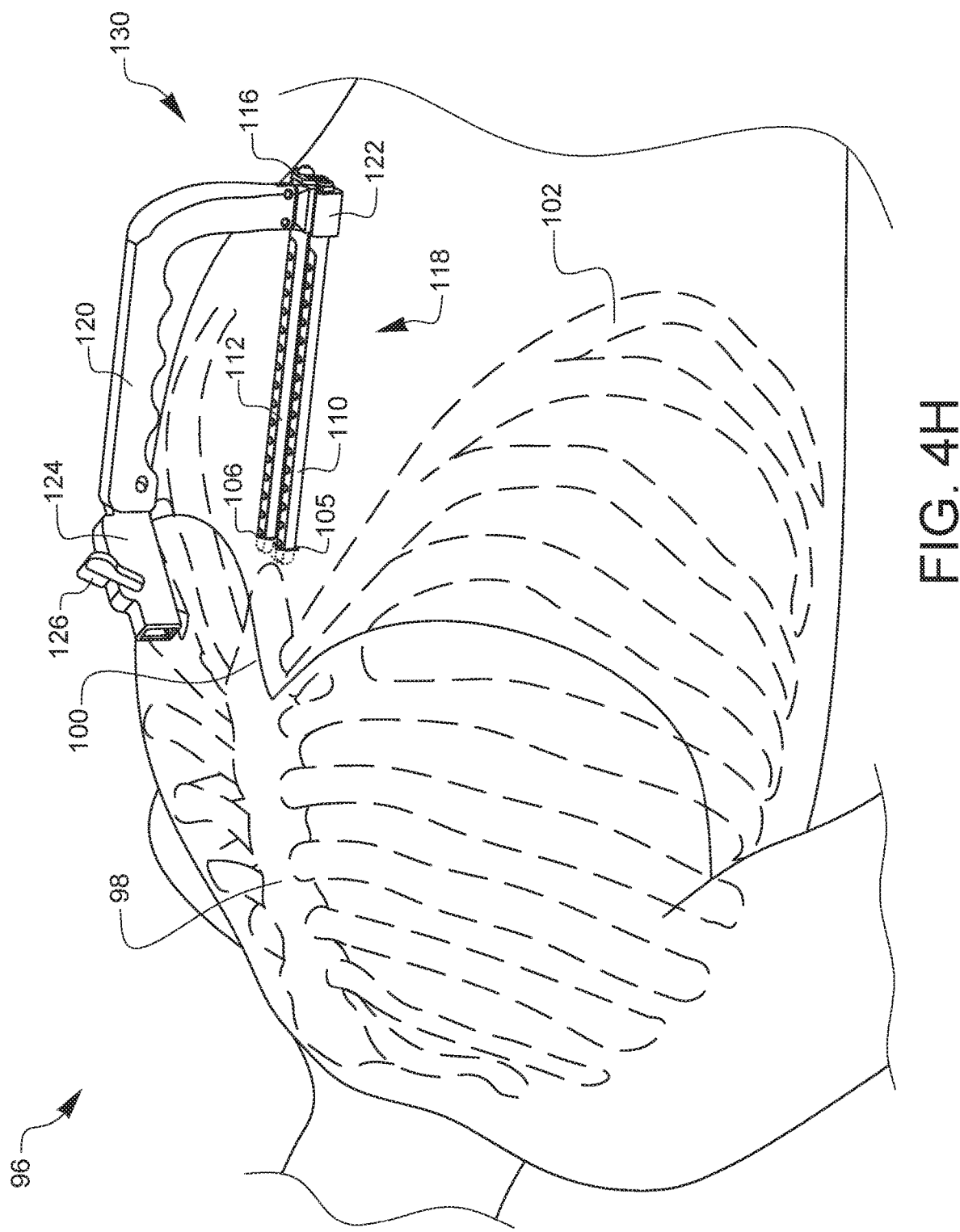
Figure 4J:
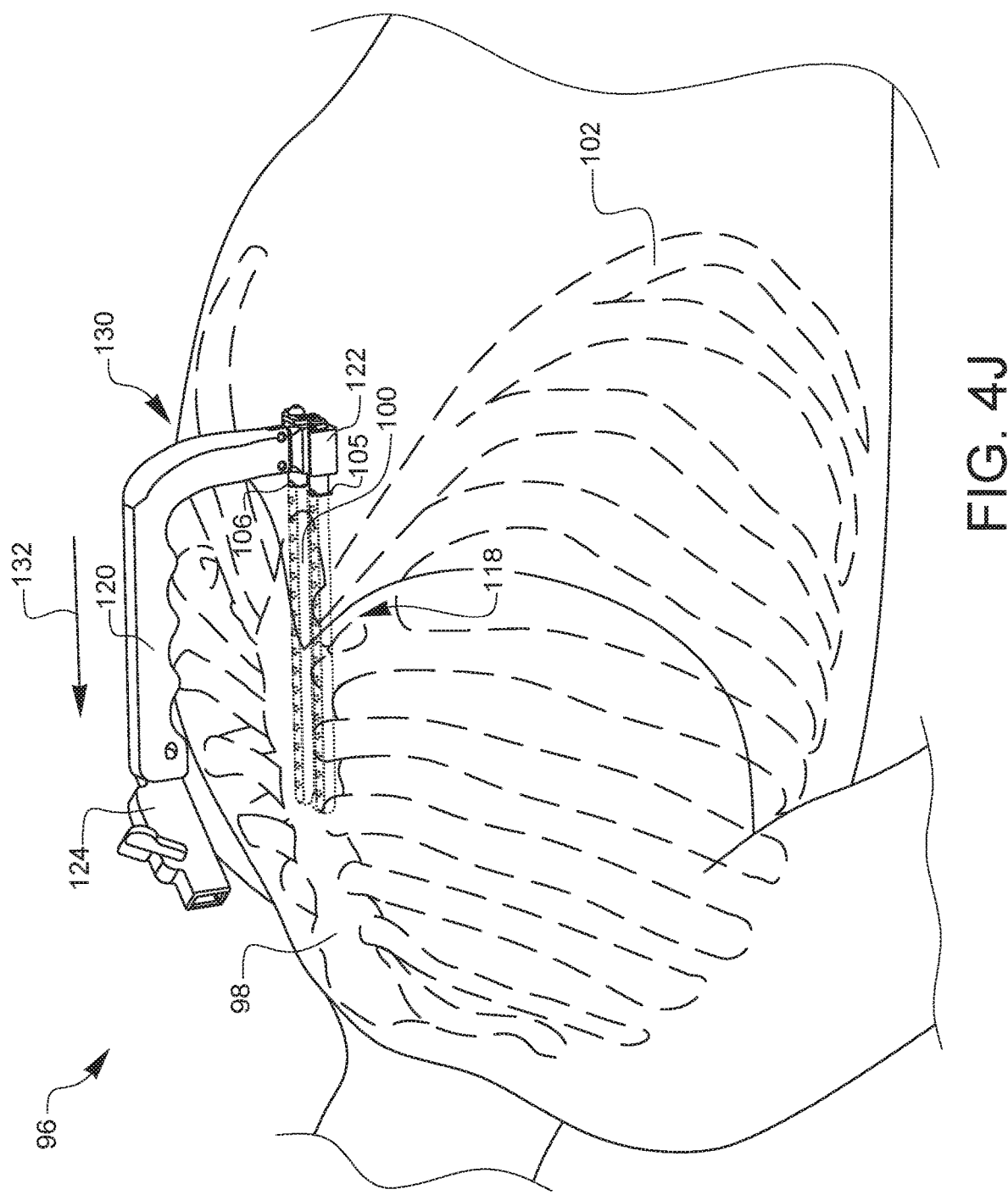
Figure 4K:
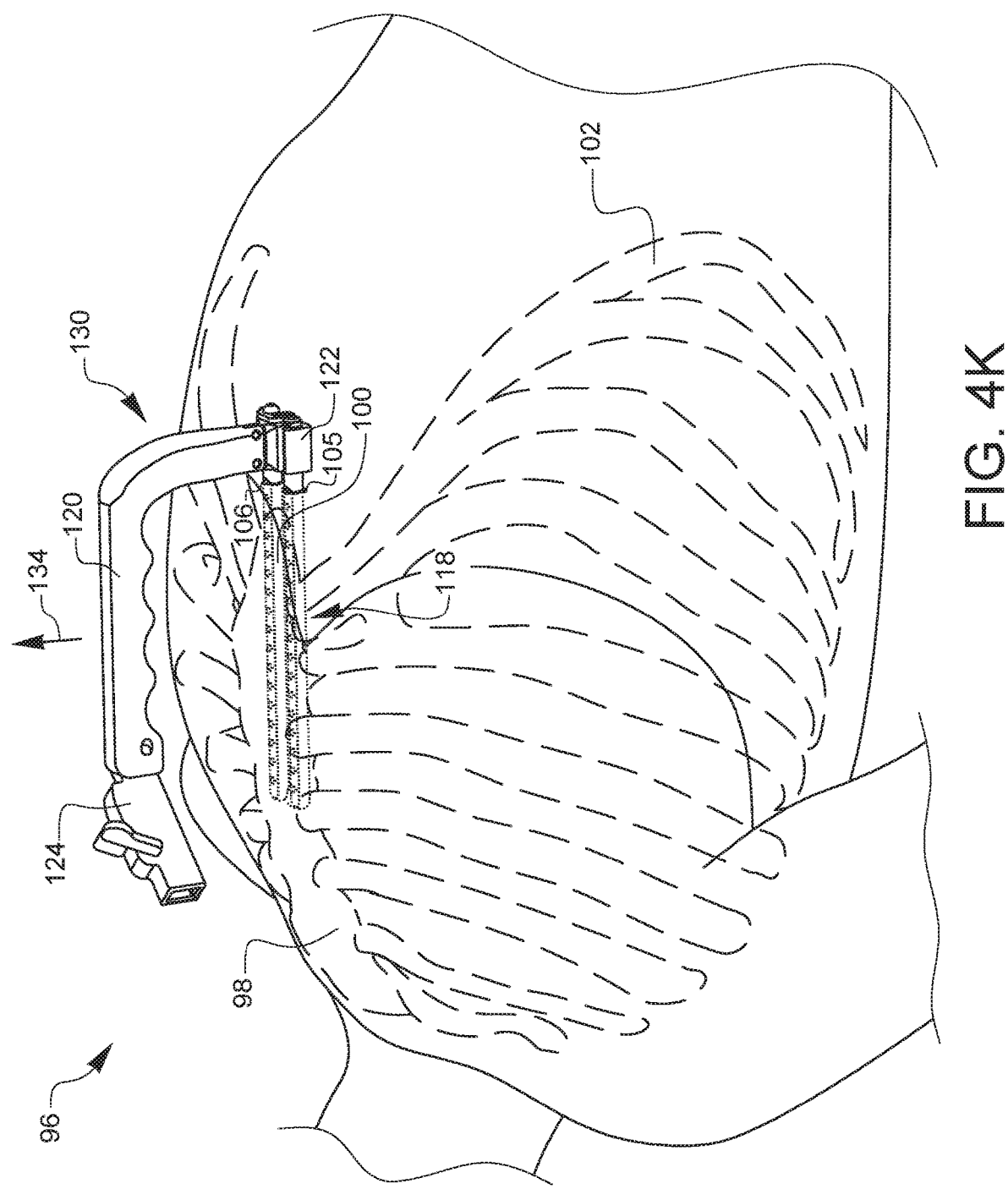
Figure 4L:
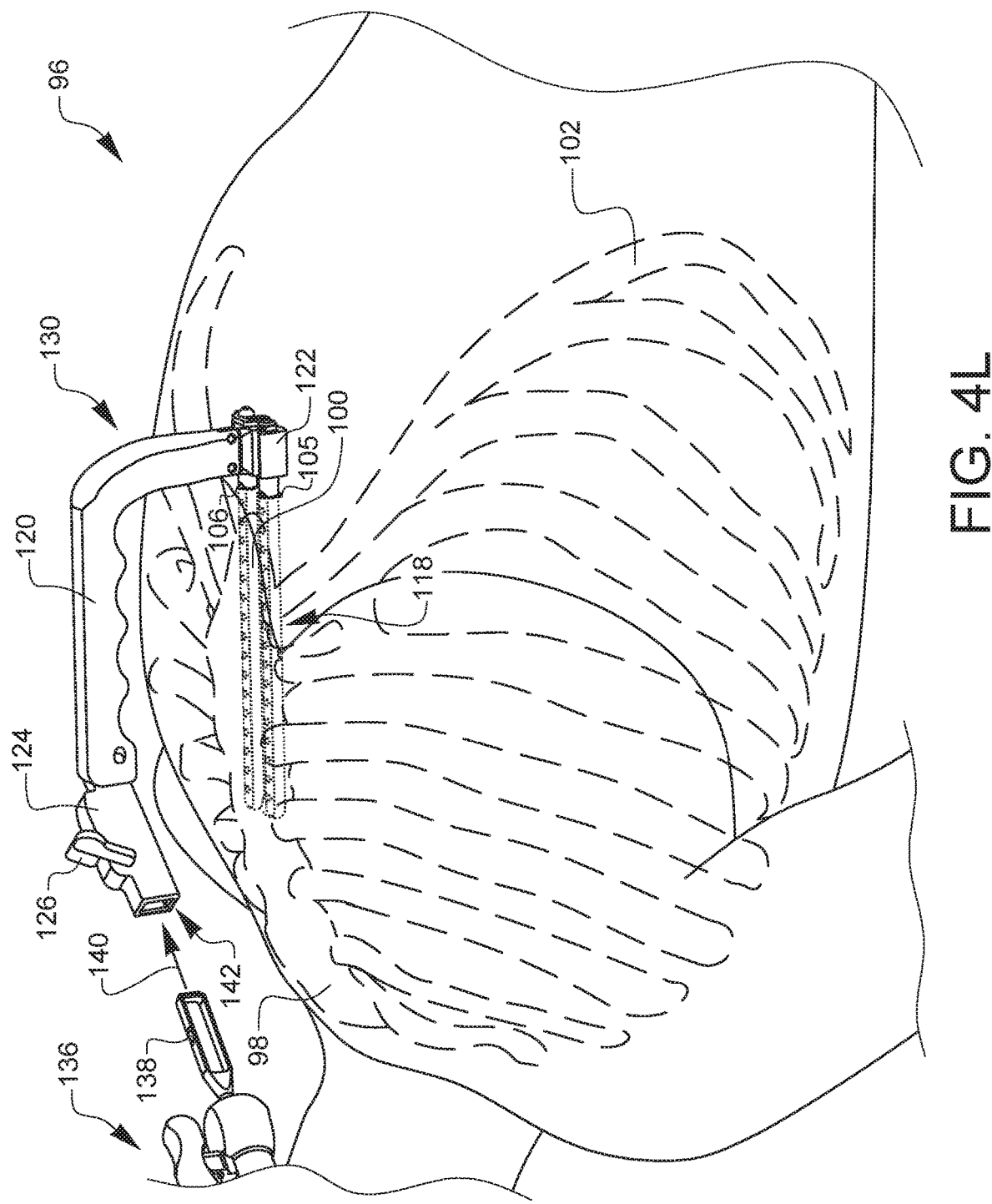
Figure 4M:
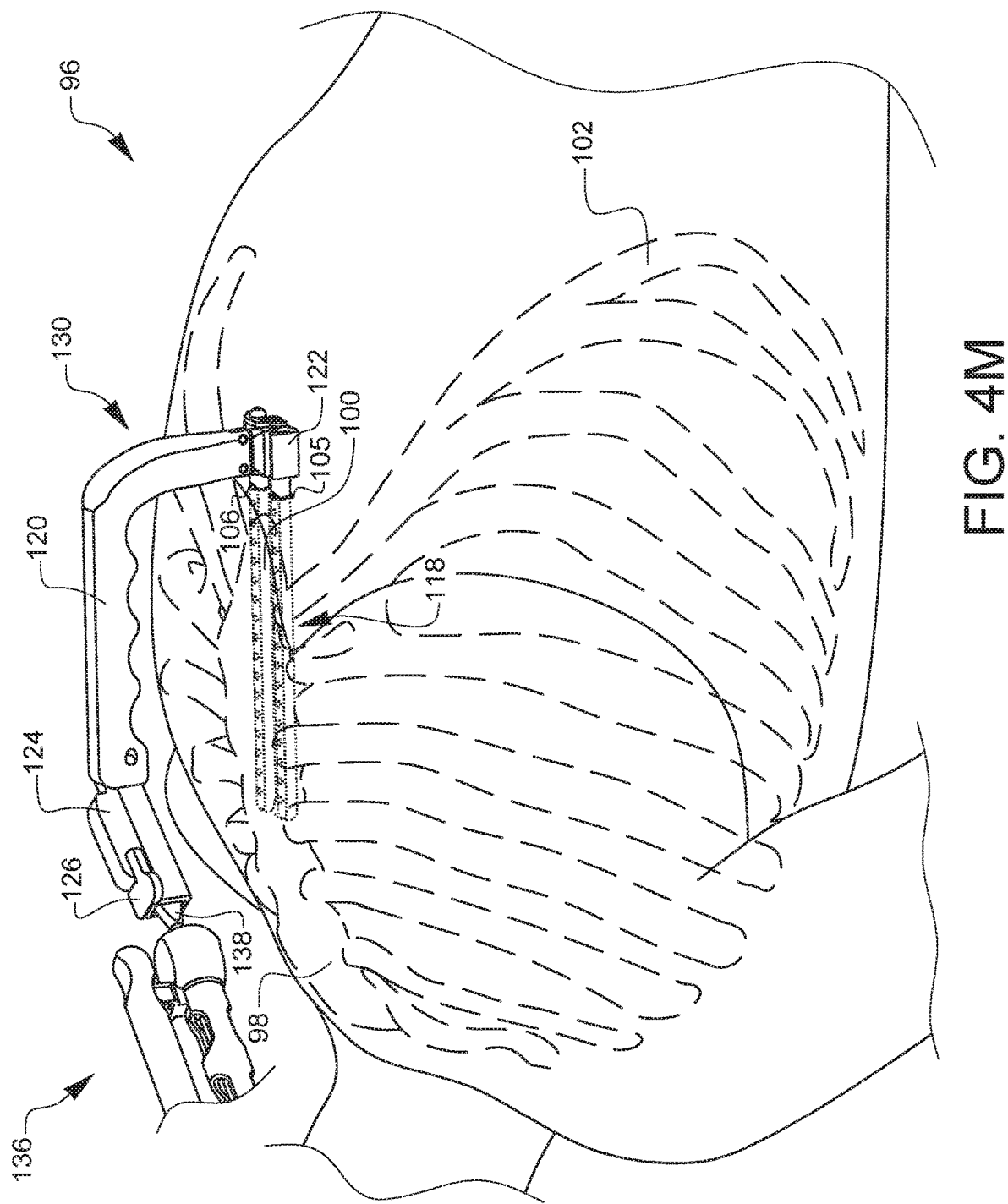

FIG. 4H illustrates the percutaneous subxiphoid lifting device 130 in place in the two incisions 105, 106 with both components, the lifter assembly 120 and the beam assembly 118, combined and engaged with the latch 116 fastened and releasably holding the lifter assembly 120 and beam assembly 118 together. FIG. 4J shows the movement of the percutaneous subxiphoid lifting device 130 in a cephalad direction 132 to push the percutaneous subxiphoid lifting device 130 below the sternum 98 and past the xiphoid 100 by a full insertion into the two incisions 105, 106. In concert with or as a result of pushing the percutaneous sub-xiphoid lifting device 130 beneath the sternum 98 and in a cephalad direction 132 or towards the head of the patient, tissue has been cleared away to gain access to a surgical area of interest. It should be noted that alternate embodiments of a percutaneous sub-xiphoid lifting device may have components or features at the distal end of the beam assembly that aid or facilitate the clearance of such tissue. A flat blade-like structure or a thin or sharpened swivel link like those described previously may be incorporated into the distal end of a percutaneous sub-xiphoid lifting device for such a purpose. Once in place past the xiphoid 100, as shown in FIG. 4K, the percutaneous subxiphoid lifting device 130 may be lifted in an anterior direction 134 providing increased subxiphoid space for a minimally invasive surgical procedure, such as the harvesting of the left internal thoracic artery (LITA) or the right internal thoracic artery (RITA). When the lifter assembly 120 is lifted in the anterior direction 134, the sternum 98 is lifted away from a diaphragm to increase space for a minimally invasive surgical procedure. As shown in FIG. 4L, once the percutaneous subxiphoid lifting device 130 is lifted a surgical equipment holder 136 is attached to the percutaneous subxiphoid lifting device 130 by inserting the end effector 138 of the surgical equipment holder 136 in direction 140 into an opening 142 on the instrument adapter 124 attached to the percutaneous subxiphoid lifting device 130. The attachment to the surgical instrument holder 136 allows for stabilization and positional fine adjustments of the percutaneous subxiphoid lifting device 130 as needed during any subsequent procedure. FIG. 4M illustrates the surgical equipment holder 136 inserted into the instrument adapter 124 attached to the percutaneous subxiphoid lifting device 130 once the percutaneous subxiphoid lifting device 130 is in the desired position. The lever lock 126 on the instrument adapter 124 is engaged, which holds and locks the percutaneous subxiphoid lifting device 130 in the surgical equipment holder 136 until it is removed.

After the percutaneous sub-xiphoid lifting device 130 has been placed in the desired position, several additional incisions can be made in the patient in a caudad direction or toward the lower end of spine relative to the existing incisions 105, 106. The purpose of these additional incisions (not shown in this view) is for the introduction and accommodation of additional instruments for continuing a minimally invasive surgical procedure as needed. For example, an endoscope, a grasping instrument or manipulation instrument, and a pair of laparoscopic scissors or a dissection instrument may be inserted into any additional incisions or ports. It shown be noted that alternate instrument adapters or surgical equipment or instrument holders may be used in other embodiments.

While the initial phases of a minimally invasive internal thoracic artery harvesting surgical procedure are shown and described herein, other surgical procedures can benefit from having minimally invasive access to spaces within the ribcage, such as epicardial lead placement and other cardiac repair procedures, and others. A minimally invasive approach to gaining access within the ribcage can facilitate patient outcome and healing, as well as reduce operating times when utilized as part of a minimally invasive surgical procedure.

Figure 5:
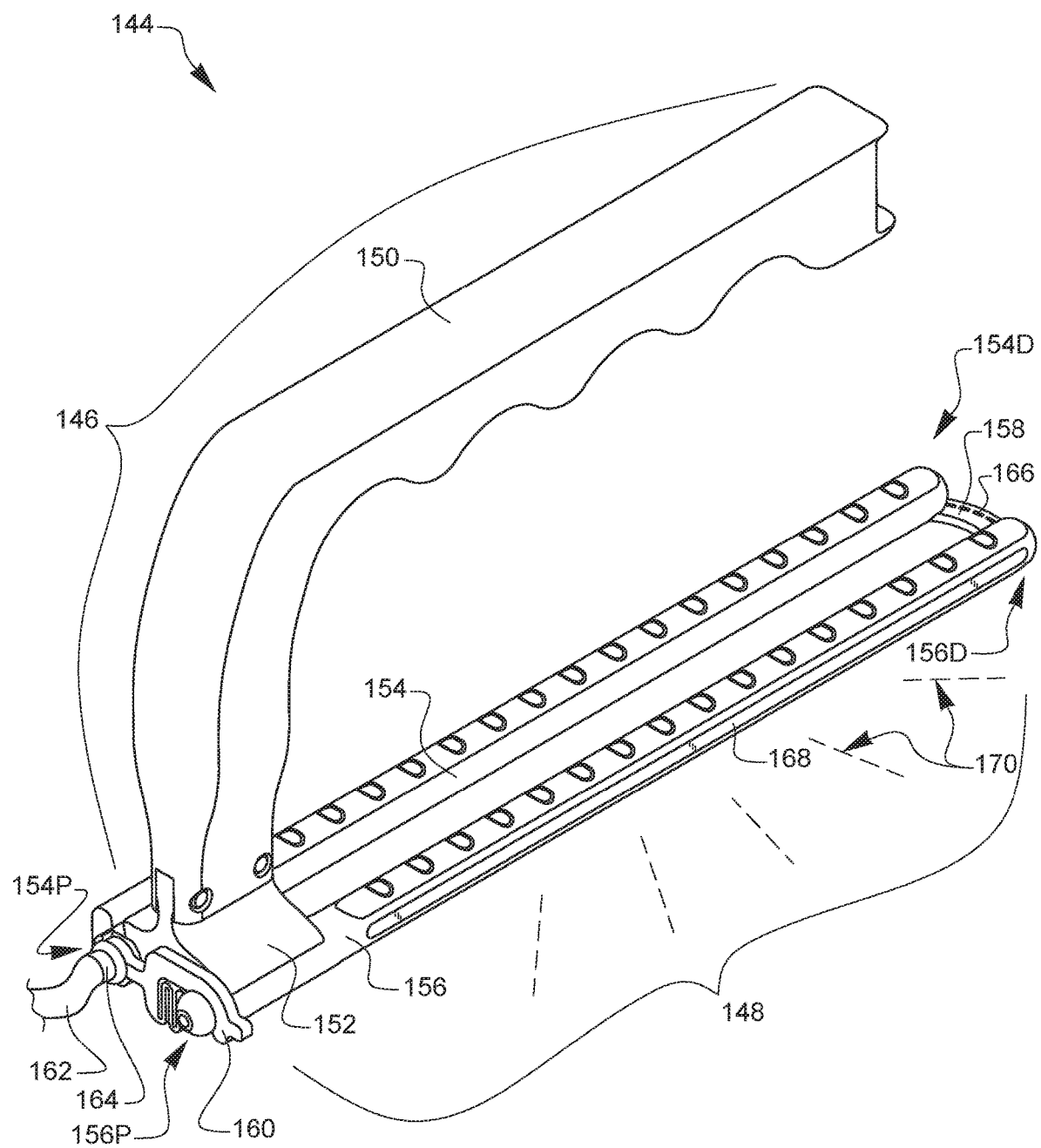
FIG. 5 is a proximal-top-right perspective view of another embodiment of a percutaneous sub-xiphoid lifting device which includes a light source.

FIG. 5 is a proximal-top-right perspective view of another embodiment of a percutaneous sub-xiphoid lifting device which includes a light source. The percutaneous sub-xiphoid lifting device 144 includes a lifter assembly 146, which includes a handle 150 and a lifter block 152. The percutaneous sub-xiphoid lifting device 144 also includes a beam assembly 148, which includes a first beam 154 and a second beam 156 connected at their respective distal ends 154D, 154D by a swivel link 158. The beam assembly 148 is configured to be releasably engaged into the lifter block 152 portion of the lifter assembly 146. The first beam 154 and the second beam 156 are pivotably coupled by the swivel link 158 connected to the distal end 154D of the first beam 154 and the distal end 156D of the second beam 156. A latch 160 is attached to the proximal end 154P of the first beam 154 and is configured to rotate or pivot around a pivoting element (not shown in this view) and latch the second beam 156 in place once the first beam 154 and the second beam 156 have been fully inserted into the lifter block 152. It should be noted that while this is one embodiment of a percutaneous sub-xiphoid lifting device 144, it is not meant to be a limiting example. Other embodiments of this device may include a beam assembly that is permanently attached to a lifter assembly or include beams that are not rotatably or pivotably coupled. While this embodiment is illustrated in a manner that allows for approximately 90-degree rotation or pivot between the first beam 154 and the second beam 156, other embodiments may pivot further than 90 degrees, for example, 180 degrees or more. Likewise, the first beam and second beams of an alternate embodiment may be coupled in a manner that allows for additional degrees of freedom of movement and may swivel in multiple directions and to further extents than 90 degrees or 180-degree angles between the first beam and the second beam. Either one or both ends of the swivel link 158 may pivot. Alternative ways of coupling the beams may also be used, such as hinges, additional beams, fixed shims, support members, or others known by those skilled in the art. Other embodiments for beams may be used in these devices as well. While the beams shown in this embodiment of a percutaneous sub-xiphoid lifting device 144 are cylindrical rods, other beams may be used in alternate embodiments, such as flat shims, rectangular beams, flat blades, or others known by those skilled in the art. The beams may also be arranged in orientations other than parallel.

The percutaneous sub-xiphoid lifting device 144 also has a light pipe 162 connected to the proximal end 154P of the first beam 154 by way of a connector 164. This light pipe 162 introduces a light source into this embodiment of a percutaneous sub-xiphoid lifting device 144 for improved visualization inside the chest cavity during a minimally invasive surgical procedure. While not shown completely in this view, the light travels from the proximal end 154P of the first beam 154 through to the distal end 154D of the first beam 154. Embedded in the swivel link 158 is a continuation of the light path 166 which brings the light path 166 through to the second beam 156. This light path 166 continues through the second beam 156 from the distal end 156D of the second beam 156 to the proximal end 156P. On the side of the second beam 156 is a lighting element 168 which is composed of a translucent or transparent material window or insert that allows light 170 to be transmitted outwardly from the second beam 156. While not shown in this view, there is a corresponding lighting element 168 on the opposite side facing outwardly from the first beam 154. Alternative embodiments may include internal or external light sources or other sources or wavelengths of light, including fiber optic, halogen, incandescent, or light-emitting diodes, as well as visible light, infrared light, or ultraviolet light, or combinations thereof.

Various advantages of a percutaneous sub-xiphoid lifting device have been discussed above. Embodiments discussed herein have been described by way of example in this specification. It will be apparent to those skilled in the art that the foregoing detailed disclosure is intended to be presented by way of example only and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A percutaneous sub-xiphoid lifting device, comprising:
a handle;
a lifter block coupled to a portion of the handle;
a first beam extending from a proximal end to a distal end along a first beam axis, wherein a first portion of the first beam at or adjacent to the proximal end of the first beam is removably coupled to a first portion of the lifter block; and
a second beam extending from a proximal end to a distal end along a second beam axis, wherein a first portion of the second beam at or adjacent to the proximal end of the second beam is removably coupled to a second portion of the lifter block, and wherein a second portion of the first beam at or adjacent to the distal end of the first beam is pivotably coupled to a second portion of the second beam at or adjacent to the distal end of the second beam; and
a latch pivotably secured to the proximal end of the first beam to releasably engage a third portion of the proximal end of the second beam to releasably secure the first portion of the second beam in the first portion of the lifter block.

2. The percutaneous sub-xiphoid lifting device of claim 1, further comprising a swivel link connecting the second portion of the first beam at or adjacent to the distal end of the first beam and the second portion of the second beam at or adjacent to the distal end of the second beam, the swivel link configured such that the second beam is pivoted up to 180 degrees relative to the first beam.

3. The percutaneous sub-xiphoid lifting device of claim 1, wherein the handle further comprises an ergonomic grip.

4. The percutaneous sub-xiphoid lifting device of claim 1, wherein the second portion of the lifter block defines a slot opening.

5. The percutaneous sub-xiphoid lifting device of claim 1, wherein the first portion of the lifter block defines a keyed opening.

6. The percutaneous sub-xiphoid lifting device of claim 1, wherein an aperture is disposed in the proximal end of the second beam.

7. The percutaneous sub-xiphoid lifting device of claim 1, wherein the first beam defines one or more flat areas near the proximal end of the first beam.

8. The percutaneous sub-xiphoid lifting device of claim 1, wherein the second beam defines one or more flat areas near the proximal end of the second beam.

9. The percutaneous sub-xiphoid lifting device of claim 1, wherein the first beam further comprises an atraumatic surface.

10. The percutaneous sub-xiphoid lifting device of claim 1, wherein the second beam further comprises an atraumatic surface.

11. The percutaneous sub-xiphoid lifting device of claim 1, further comprising an instrument adapter coupled to the handle.

12. The percutaneous sub-xiphoid lifting device of claim 1, further comprising:
a light source coupled to the proximal end of the first beam.

13. The percutaneous sub-xiphoid lifting device of claim 12, wherein the light source is selected from a group consisting of halogen, light-emitting diode, ultraviolet, and infrared.

14. The percutaneous sub-xiphoid lifting device of claim 1, wherein the first beam axis is linear and the second beam axis is linear.

* * * * *